US012629215B2

(12) United States Patent
Schöpp et al.

(10) Patent No.: US 12,629,215 B2
(45) Date of Patent: May 19, 2026

(54) BONE CLAMP AND SURGICAL TRACKING SYSTEM COMPRISING THE BONE CLAMP

(71) Applicant: Stryker European Operations Limited, Carrigtwohill (IE)

(72) Inventors: Hans Schöpp, Freiburg (DE); Oliver Weede, Freiburg (DE); Inderjeet Singh Bedi, Pratap Pura (IN); Bharath S, Bangalore (IN)

(73) Assignee: Stryker European Operations Limited, Carrigtwohill (IE)

( * ) Notice: Subject to any disclaimer, the term of this patent is extended or adjusted under 35 U.S.C. 154(b) by 210 days.

(21) Appl. No.: 18/372,918

(22) Filed: Sep. 26, 2023

(65) Prior Publication Data

US 2024/0099782 A1    Mar. 28, 2024

(30) Foreign Application Priority Data

Sep. 28, 2022    (EP) .................................... 22198383

(51) Int. Cl.
*A61B 34/20*        (2016.01)
*A61B 17/56*        (2006.01)
        (Continued)

(52) U.S. Cl.
CPC .............. *A61B 34/20* (2016.02); *A61B 17/56* (2013.01); *A61B 2017/0092* (2013.01); (Continued)

(58) Field of Classification Search
CPC ............ A61B 17/7047; A61B 17/7076; A61B 17/862; A61B 17/8695
See application file for complete search history.

(56) References Cited

U.S. PATENT DOCUMENTS 6,569,169 B2    5/2003  De La Barrera et al.
9,737,235 B2    8/2017  Hartmann
        (Continued)

FOREIGN PATENT DOCUMENTS

DE      102013108678 A1    3/2015
EP          1197185 A1    4/2002
EP          1523951 B1    10/2012

OTHER PUBLICATIONS

English language abstract and machine-assisted English translation for DE 10 2013 108 678 A1 extracted from espacenet.com database on Sep. 27, 2023, 23 pages.

(Continued)

*Primary Examiner* — Zade Coley
(74) *Attorney, Agent, or Firm* — Howard & Howard Attorneys PLLC

(57)        ABSTRACT

A bone clamp including two or more clamping members configured to clampingly receive a bone therebetween. The bone clamp further includes a basis supporting at least two of the clamping members at a first distance to each other. At least one of the at least two clamping members has a body and is rotatably supported by the basis. The at least one rotatably supported clamping member has a bone engaging structure extending helically along at least a part of a length of its body. The bone engaging structure is configured to engage a side surface of the bone upon rotation of the at least one rotatably supported clamping member. Depending on the direction of the rotation, the rotatably supported clamping member advances along the side surface of the bone either in a downward direction for mounting the bone clamp or in an upward direction for dismounting the bone clamp.

19 Claims, 9 Drawing Sheets

(51) Int. Cl.
  *A61B 17/00* (2006.01)
  *A61B 90/00* (2016.01)
(52) U.S. Cl.
  CPC . *A61B 2017/564* (2013.01); *A61B 2034/2072*
    (2016.02); *A61B 2090/3916* (2016.02); *A61B*
    *2090/3991* (2016.02)

(56) References Cited

U.S. PATENT DOCUMENTS

| | | | |
|---|---|---|---|
| 10,932,837 B2 * | 3/2021 | Moctezuma De La Barrera | ........ A61B 17/8028 |
| 11,116,576 B2 | 9/2021 | Theodore et al. | |
| 2005/0171557 A1 | 8/2005 | Shoham | |
| 2007/0010817 A1 * | 1/2007 | de Coninck | ....... A61B 17/8047 606/292 |
| 2009/0012532 A1 * | 1/2009 | Quaid | ................ A61B 17/1764 128/898 |
| 2010/0204714 A1 * | 8/2010 | Shoham | ................. A61B 34/72 606/130 |
| 2014/0257288 A1 * | 9/2014 | Chang | ................. A61B 17/645 606/59 |
| 2018/0147021 A2 * | 5/2018 | Fleig | ..................... A61B 34/20 |
| 2018/0263670 A1 * | 9/2018 | Moctezuma De La Barrera | ........ A61B 17/8061 |
| 2018/0311011 A1 | 11/2018 | Van Beek et al. | |
| 2021/0346117 A1 * | 11/2021 | Poltaretskyi | ........... A61B 90/36 |
| 2022/0265354 A1 | 8/2022 | Kayal et al. | |

OTHER PUBLICATIONS

English language abstract for EP 1 197 185 A1 extracted from espacenet.com database on Sep. 27, 2023, 2 pages.

* cited by examiner

1

BONE CLAMP AND SURGICAL TRACKING SYSTEM COMPRISING THE BONE CLAMP

PRIORITY CLAIM

This application claims priority under 35 U.S.C. § 119 to European Patent Application No. 22198383.6, filed Sep. 28, 2022, the entire contents of which are hereby incorporated by reference.

TECHNICAL FIELD

The present disclosure generally relates to a bone clamp. In some versions, the bone clamp is configured to support an auxiliary device such as a tracker of a surgical tracking system. Also presented is a surgical tracking system comprising the bone clamp.

BACKGROUND

Bone clamps are used for many purposes. In some cases, bone clamps help to join bone parts. In other cases, bone clamps support an auxiliary device assisting in a surgical intervention. An example of such an auxiliary device is a tracker of a surgical tracking system. Bone clamps can be used to attach the tracker to a bone that is to be tracked during a surgical intervention. Surgical tracking techniques are commonly used for assisting surgeons in a surgical navigation context in which a bone is tracked using a dynamic reference frame.

To provide a high tracking accuracy and, thus, the desired surgical results, the tracker has to be firmly attached to the bone that is to be tracked. One possibility in this regard is to use a bone clamp configured to support the tracker. Conventional bone clamps comprise clamping jaws which are pressed against opposite bone surfaces (see the bone clamp described in EP 1 197 185 A). Another possibility is the use of bone screws to directly attach the tracker to bone.

Each of these attachment options has its advantages and disadvantages. The use of bone screws generally leads to a more stable fixation of the tracker compared to the use of clamping jaws. Inserting bone screws into bone is, however, an invasive procedure that injures tissue and bone. While the use of conventional bone clamps is generally less invasive than the use of bone screws, the clamping jaws still need to be placed over a significant area on both sides of a bone, and teeth of the jaws must penetrate deep enough into the bone to ensure a stable hold. Larger jaws usually also provide a larger contact area and thus an improved grip. As a result, the jaw surfaces can be of considerable size. On the other hand, the tissue between the clamp and the bone is damaged when the clamp is mounted. Thus, the larger the jaw surfaces, the more invasive is the mounting of the clamp.

Furthermore, conventional bone clamps are largely made of non-radiolucent materials such as stainless steel. Such clamps thus create large artifacts on an intraoperatively acquired image, such as an X-ray image.

SUMMARY

There is a need for a device and a system addressing one or more of the above, or other, problems.

According to one aspect, a bone clamp comprising two or more clamping members configured to clampingly receive a bone therebetween is provided. The bone clamp further comprises a basis supporting at least two of the clamping members at a first distance to each other. At least one of the at least two clamping members has a body and is rotatably supported by the basis. The at least one rotatably supported clamping member has a bone engaging structure extending helically along at least a part of a length of its body. The bone engaging structure is configured to engage a side surface of the bone upon rotation of the at least one rotatably supported clamping member.

In some variants, depending on the direction of the rotation, the rotatably supported clamping member may be configured to advance along the side surface of the bone either in a downward direction for mounting the bone clamp or in an upward direction for dismounting the bone clamp.

The bone clamp may be used for various purposes, such as joining bone parts. Additionally, or in the alternative, the bone clamp may be used as a support structure for an auxiliary device used during a surgical intervention. The bone clamp may be configured to be detachably mounted to bone.

The basis may be substantially be made of a solid material. The base may be substantially made of a radiolucent material (e.g., from a polymeric material). The body of one or more of the clamping members may be substantially cylindrical (possibly including a certain tapering in a direction towards the bone, wherein the tapering is less than 20°, in particular less than 10° relative to a longitudinal axis of the body). One or more of the clamping members may be integrally formed with the basis.

The bone engaging structure may be a continuous thread or a thread-like structure. The thread-like structure may comprise discontinuous, spaced-apart protrusions arranged along a helical path. The thread or thread-like structure may have a self-tapping configuration. The at least one rotatably supported clamping member may be a self-tapping bone screw. The thread or thread-like structure may be configured to cut into a side surface of a bone upon rotation of the at least one rotatably supported clamping member. The thread or thread-like structure may have at least one of a diameter between 1 mm and 7 mm, in particular between 3 mm and 5 mm, a height between 5 mm to 50 mm, in particular between 10 mm and 40 mm, and a pitch between 0.5 mm and 5 mm, in particular between 1 mm and 4 mm.

At least one of the at least two clamping members may have a body without any bone engaging structure and, for example, form a pin. Additionally or alternatively, at least one of the at least two clamping members may be formed as a planar or curved plate (with or without any bone penetrating structures on a surface facing a side surface of the bone received by the bone clamp). Such a clamping member without any bone engaging structure may be configured immovable relative to the base (e.g., integral with the base). In some versions, such a clamping member may comprise teeth on a bone contacting surface thereof.

In one variant, the at least two clamping members may each have a body that is rotatably supported by the basis and has a bone engaging structure extending helically along at least a part of a length of its body. The at least two rotatably supported clamping members may be supported at the first or a second distance from each other. In the case of three or more clamping members, a first and a second rotatably supported clamping member may be supported at the first distance and the first and at least one third (e.g., non-rotatable) clamping member may be supported at the second distance. The first and the second clamping members may be arranged on a first side of the bone and the at least one third clamping member may be arranged on a second side of the bone opposite to the first side. At least one of the first distance and the second distance may be predefined. At least one of the first distance and the second distance may be fixed. The first distance may be smaller or larger than the second distance.

The first distance may be selected such that the at least two clamping members can be brought into a clamping engagement with a bone from at least a first side and a second side of the bone. The second side may be opposite to the first side. For example, the bone clamp may comprise three, four or more clamping members configured to be brought into a clamping engagement with a bone from two, three or four sides. The size of the bone may be previously known or determined. For example, the bone clamp may be dimensioned to be clamped to a vertebra, in particular a spinous or transverse process of the vertebra. In another example, the bone clamp may be dimensioned to be clamped to a bone of a pelvis or a collar bone or another bone.

The second distance may be selected based on a side length of the bone, in particular of the first or the second side of the bone. Two clamping members arranged on the same side of the bone may be spaced apart by the second distance.

In one variant, at least one of the rotatably supported clamping members may be located on the first side of the bone and at least another rotatably supported clamping members may be located on the second side of the bone. The bone engaging structures of the rotatably supported clamping members located on the first and second sides of the bone may be configured to engage the respective one of the first and second sides of the bone upon rotation of the respective rotatably supported clamping member. In some implementations, the bone clamp comprises at least three or four rotatable clamping members, with at least one or two rotatable clamping member being located on the first side and at least two rotatable clamping members being located on the second side.

In one variant, each of the at least two clamping members has a longitudinal axis, with the longitudinal axes of the at least two clamping members extending substantially parallel to each other. A substantially parallel extension may, for example, be given if the axes (or their extensions) enclose an angle of less than +/−10°.

In one variant, the bone clamp may be configured to move in a direction parallel to the longitudinal axes of the at least two rotatably supported clamping members upon simultaneous rotation thereof. In this variant, upon rotation of the rotatably supported clamping members, the clamping members may not individually move relative to the basis along the longitudinal axes towards the bone. Instead, the whole bone clamp moves in a direction parallel to the longitudinal axes. In such a variant, the rotatably supported clamping members may be infinitely rotatable in the basis without advancing relative to the basis.

In another variant, each of the at least one rotatably supported clamping member is configured to move relative to the basis in a direction parallel to the longitudinal axis of its body, when rotated. Upon rotation, the at least one rotatably supported clamping member may thus advance relative to the base. In this variant, multiple rotatably supported clamping members, if present, may be rotated non-simultaneously.

In some implementations, the bone clamp may comprise a combination of one or more rotatably supported clamping members that are configured to move along their respective longitudinal axes relative to the basis when rotated, and one or more rotatably supported clamping members that are configured not to move along their respective longitudinal axes relative to the basis when rotated.

The body of the at least one rotatably supported clamping member may comprise a distal portion configured to receive at least a part of an actuation member configured to rotate the at least one rotatably supported clamping member. The distal portion may comprise a torque-receiving structure (e.g., it may be formed like a screwhead). In particular, the distal portion may comprise a slot, a cross-slot, a hexagonal socket or a socket having any other geometrical form suited to receive an actuation member capable of generating or transmitting a torque. The basis may be formed to support the rotatably supported clamping member in such a way that the distal portion does not extend beyond the basis.

The body of the at least one rotatably supported clamping member may comprise a tapering proximal portion. The tapering portion may form a pointed or a rounded tip. The body of the at least one rotatably supported clamping member may further comprise a substantially cylindrical portion adjacent to the tapering proximal portion. In some implementations, the bone engaging structure extends over at least a portion of the tapering proximal portion and (e.g., an adjacent) portion the substantially cylindrical portion.

In one variant, the basis may be made of radiolucent material (e.g., a polymer). In this variant, only the clamping members of the bone clamp may be radiopaque (e.g., the clamping members may be made from metal). As a result, the size of artifacts in an interoperative scan (e.g., an x-ray image) of a patient anatomy with the bone clamp mounted thereon may be reduced in comparison to common bone clamps.

The bone clamp may comprise a gear unit. The gear unit may have a single torque input structure and a torque output structure for each of two or more of the rotatably supported clamping members to simultaneously rotate each of the rotatably supported clamping members in response to an input torque. Each torque output structure may comprise an actuation member for actuating a rotatably supported clamping member. The single torque input structure and the torque output structures may be connected via an epicyclic gear train, such as a planetary gearset. The gear unit may thus enable a comfortable way to simultaneously actuate multiple rotatably supported clamping members. Simultaneously actuating multiple rotatably supported clamping members may result in a faster way of mounting and dismounting the bone clamp compared to an individual actuation of each rotatably supported clamping member.

In one variant, the bone clamp may comprise an interface configured for releasably engaging the gear unit, or vice versa. The interface may comprise at least one fastening member configured to releasably engage at least one complementary fastening member of the gear unit (or vice versa). For example, the fastening members may comprise at least one of complementary snap fit connections, screws and complementary threads.

The bone clamp may comprise a guiding member or an interface for receiving the guiding member. The interface may be configured to releasably receive the guiding member. The guiding member may comprise a guiding tube for each of the at least one rotatably supported clamping members, each guiding tube being configured for guiding an actuation member (such as a screw driver) to the respective rotatably supported clamping member.

The bone clamp may support, or may be configured to support, an auxiliary device. The auxiliary device may be a tracker of a surgical tracking system. The tracker may comprise one or more trackable elements. The configuration of the trackable elements depends on the nature of the tracking system, so that the tracker may be an optic tracker or an electromagnetic tracker. As such, the trackable elements may take the form of passive or active optical markers (e.g., light emitting diodes, LEDs, emitting in the visible or infrared spectrum), electromagnetic field sensors (e.g., coils), and so on. In some variants, the bone clamp comprises an interface configured to support the tracker. The interface may be configured to releasably receive the tracker. The interface may be configured to generate a clamping force (see, e.g., EP 1 197 185 A) or to be based on a form fit (e.g., when the interface is provided by the guiding member).

According to another aspect, a surgical tracking system is provided. The surgical tracking system comprises the bone clamp as described herein. The surgical tracking system further comprises a tracker (e.g., detachably) supported by the bone clamp and a sensor system configured to detect the tracker supported by the bone clamp. The tracker may be an optical tracker and the sensor system may comprise an optical camera.

BRIEF DESCRIPTION OF THE DRAWINGS

Further features and advantages of the bone clamp and the surgical tracking system presented herein are described below with reference to the accompanying drawings, in which.

DETAILED DESCRIPTION

Figure 1:
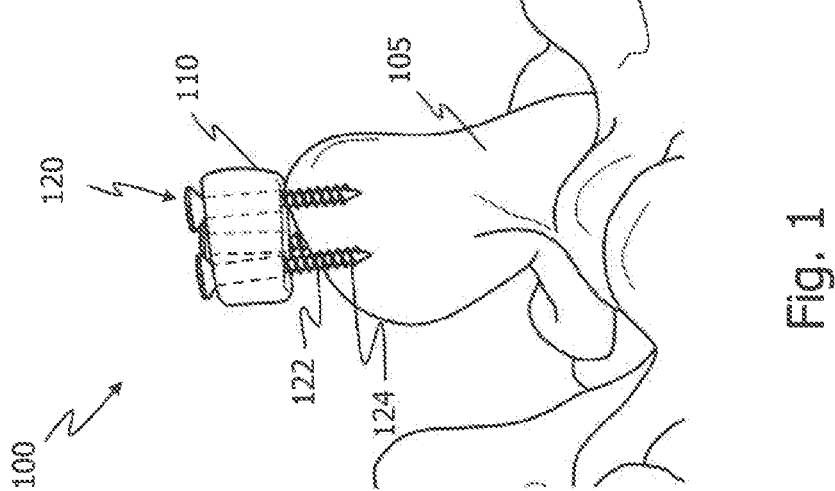
FIG. 1 illustrates a schematic representation of a bone clamp that is clamped to bone.

In the following description, for purposes of explanation and not limitation, specific details are set forth in order to provide a thorough understanding of the present disclosure. It will be apparent to one skilled in the art that the present disclosure may be practiced in other embodiments that depart from these specific details.

The same reference numerals are used to denote the same or similar components.

FIG. 1 illustrates a schematic representation of a bone clamp 100 clamped to a bone 105. In the example of FIG. 1, the bone 105 is a transverse process of a vertebra. The bone clamp 100 comprises a basis 110 and three clamping members 120, each rotatably supported by the basis 110. The basis 110 is made from a solid, polymeric and radiolucent material.

Each of the rotatably supported clamping members 120 comprises a substantially cylindrical body 122 extending along a longitudinal axis thereof. Each of the clamping members 120 further comprises a bone engaging structure 124 extending helically along at least a part of a length of its substantially cylindrical body 122. The bone engaging structures 124 shown in FIG. 1 form a thread extending along a part of the length of the substantially cylindrical bodies 122. The thread may have a self-tapping configuration. The clamping member bodies 122 may be derived from bone screws.

In some implementations, the clamping members 120 are infinitely rotatable in the basis 110 (i.e., without being advanced relative to the basis 110). In such implementations, one or more (e.g., all) of the clamping members 120 may comprise a non-threaded portion between its head and its threaded portions. This non-threaded portion may then be rotatably supported in the basis 110. In other implementations, the basis 110 may comprise a counter-thread (not shown) for at least one of the bone engaging structures 124 (or for another thread type provided between a head of the clamping member 120 and the corresponding bone engaging structure). The counter-thread enables the corresponding at least one clamping member 120 to move relative to the basis 110 in a direction parallel to the longitudinal axis of its body 122 upon rotation thereof. Each clamping member 120 may be actuated, i.e., rotated individually.

As further shown in FIG. 1, one of the rotatably supported clamping members 120 is located at a first side of the transverse process (i.e., the back side of the transverse process in the view of FIG. 1). The other two rotatably supported clamping members 120 are located at an opposite second side of the transverse process, i.e., the front side of the transverse process.

The rotatably supported clamping members 120 located on the first and second sides of the transverse process are spaced apart from each other in such a way that the respective bone engaging structure 124 engages the respective surfaces of the first and second sides of the transverse process (e.g., for about 0.5 to 3 mm). As a result, the transverse process is clampingly engaged by the bone clamp 100.

Utilizing rotatably supported clamping members 120 reduces the invasiveness compared to common bone clamps or bone screws that are fully (i.e., over 360° of their circumference) screwed into bone. Further, the basis 110 may be made of translucent material. As a result, the size of artifacts in surgical image data will be reduced.

Figure 2:
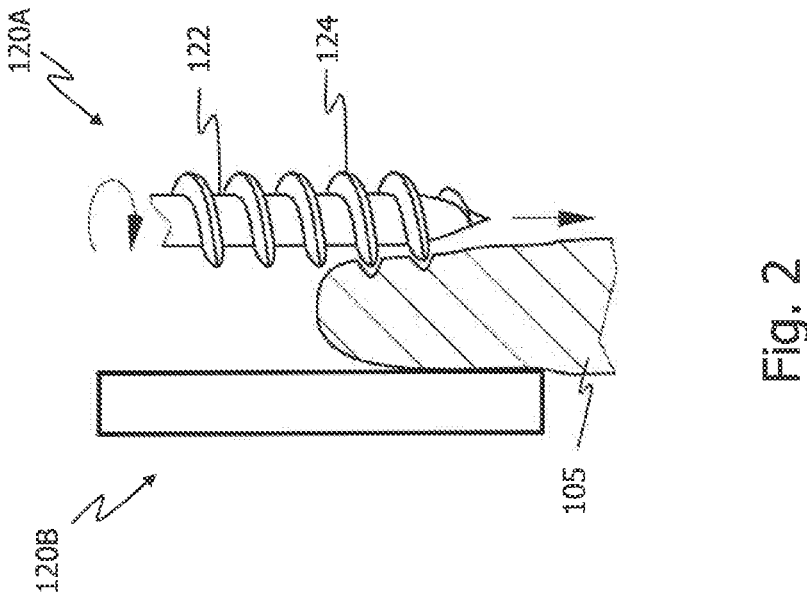
FIG. 2 illustrates a schematic representation of an interaction between clamping members of a bone clamp and bone.

FIG. 2 illustrates a schematic representation of an interaction between clamping members 120 of a bone clamp 100 with bone 105. A first clamping member 120 shown on the right side of the bone 105 is a rotatably supported clamping member 120A as described with reference to FIG. 1. Upon rotation of the rotatably supported clamping member 120A, the bone engaging structure 124 engages a surface of a side of the bone 105. Depending on the direction of the rotation, the rotatably supported clamping member 120A advances along the surface of the bone 105 either in a downward direction for mounting the bone clamp 100 or in an upward direction for dismounting the bone clamp 100.

A second clamping member 120B shown on the left side of the bone 105 does not comprise a bone engaging structure 124 in the example illustrated in FIG. 2. The clamping member 120B may form a rod or a plate-like structure and may be integral with the basis.

The clamping member 120B may comprise one or more bone piercing structures such as teeth (not shown) configured to pierce the left side of the bone, e.g., prior to or upon advancing of the first clamping member 120 along the right side of the bone. In some variants, the clamping member 120B is first brought into firm abutment with one side of the bone 105. Then, the rotatably supported clamping member 120A is actuated and advances relative to the basis in a downward direction (as illustrated by the straight arrow in FIG. 2).

Figure 3A:
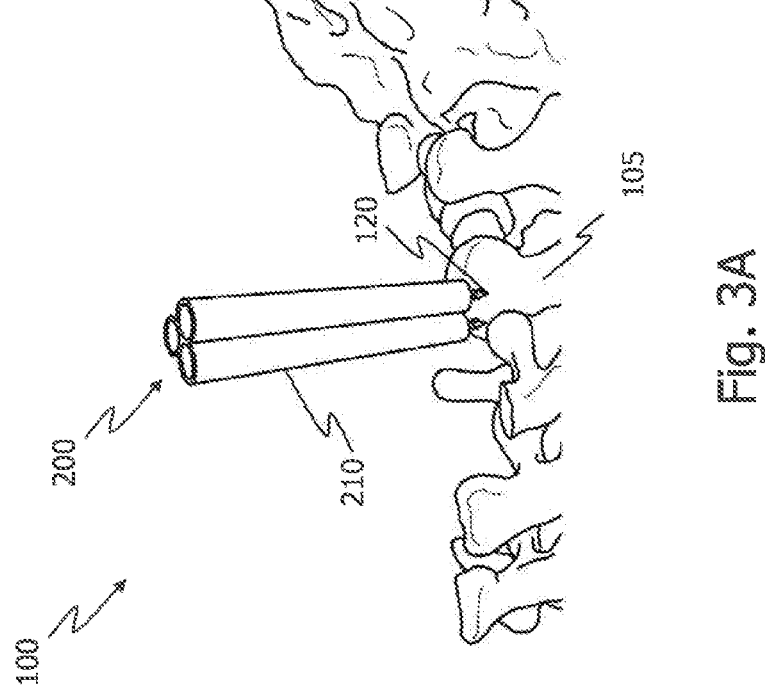
FIG. 3A illustrates a schematic representation of a bone clamp comprising a guiding member.

FIG. 3A illustrates a schematic representation of a bone clamp 100 comprising three rotatably supported clamping members 120 and a guiding member 200. The longitudinal axes of the bodies 122 of the clamping members 120 extend substantially in parallel directions (with angular deviation of +/-10° or less). The guiding member 200 comprises three guiding tubes 210, i.e., one guiding tube 210 for each of the rotatably supported clamping members 120. Each guiding tube 210 is associated with a different one of the rotatably supported clamping members 120 in that the guiding tube 210 is formed as a substantially hollow-cylindric sleeve extending co-axially relative to the body 122 of the associated clamping member 120.

The guiding tubes 210 are configured for guiding an actuation member (not shown) to the head of each of the rotatably supported clamping members 120. Each head comprises a torque-receiving structure to be driven by the actuation member. Since the rotatably supported clamping members 120 extend in parallel directions, simultaneous actuation (i.e., simultaneous rotation) of the clamping members 120 is facilitated. In case of simultaneous actuation, the bone clamp 100 is configured to move in a direction parallel to the longitudinal axes of the bodies 122 of the clamping members 120. In other words, no relative translational movement between the basis 110 and the clamping members 120 takes place upon simultaneous actuation of the clamping members 120.

In another example, the bone clamp 100 comprises an interface (not shown) for removably receiving the guiding member 200. A removable guiding member 200 may lead to a less obstructed surgical area, which results in better view and less obstructions for a surgeon. Further, cleaning of the bone clamp 100 and the guiding member 200 may be facilitated and reusability may be improved.

Figure 3B:
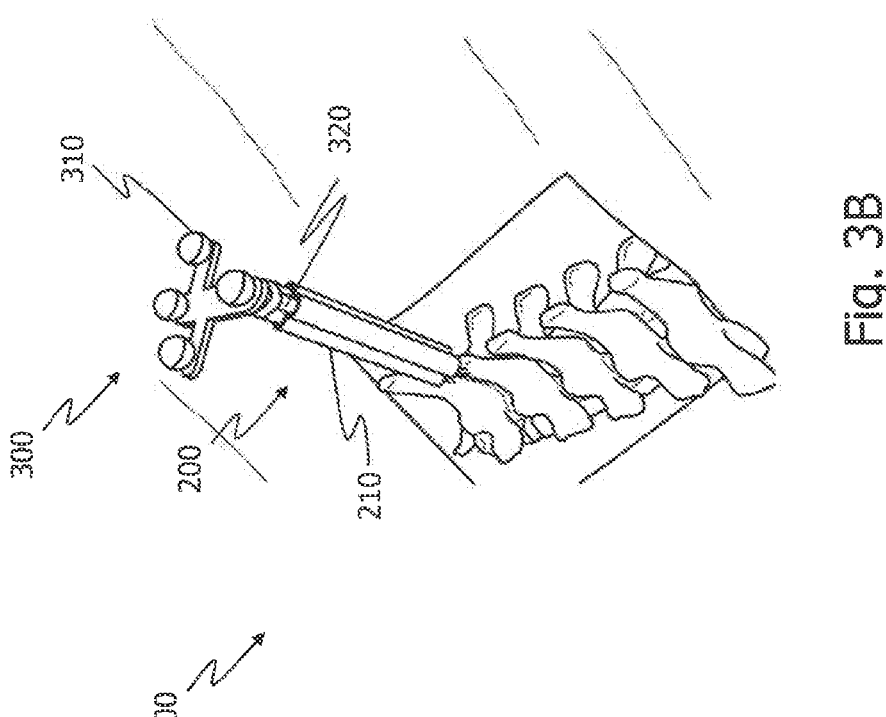
FIG. 3B illustrates a schematic representation of the bone clamp of FIG. 3A with an optical tracker mounted to the guiding member.

FIG. 3B illustrates a schematic representation of the bone clamp 100 of FIG. 3A with an optical tracker 300 attached to the guiding member 200. The optical tracker 300 comprises four passive markers 310 in the form of reflective spheres and is releasably attached to the guiding member 200. For attachment to the guiding member 200, the tracker 300 comprises three cylindrical protrusions 320 configured to be received by the guiding member 200 in a form-fitting manner.

Figure 4:
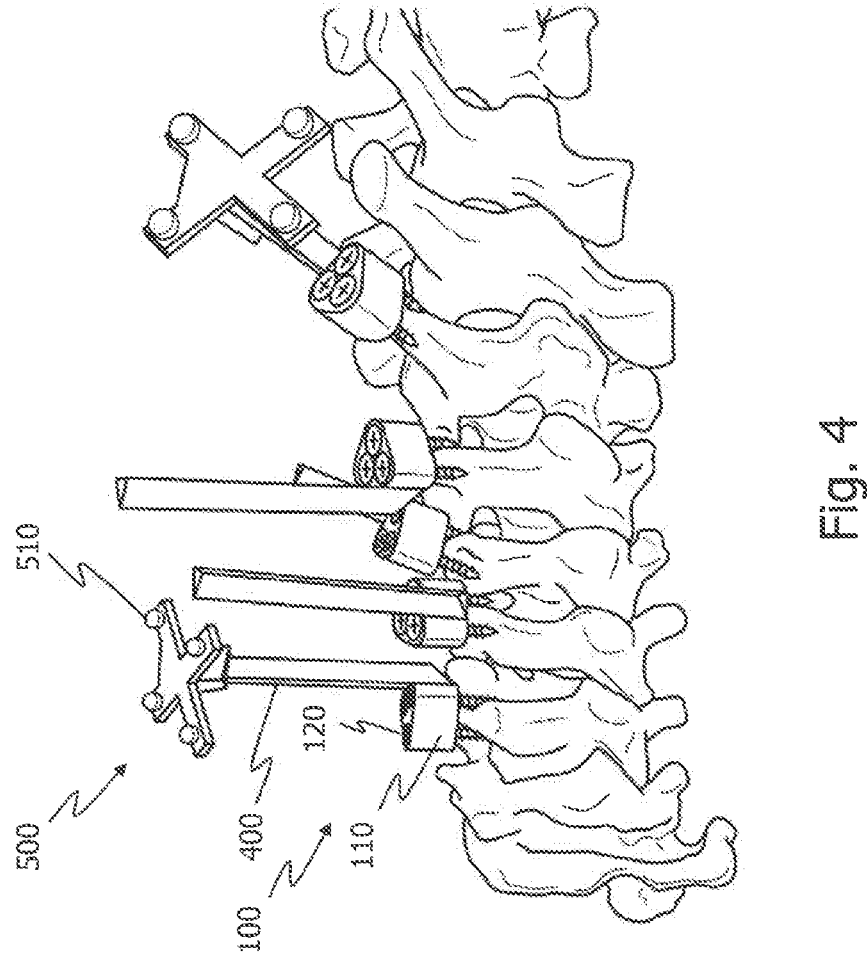
FIG. 4 illustrates a schematic representation of multiple bone clamps, each mounted to a different vertebra.

FIG. 4 illustrates a schematic representation of multiple bone clamps 100, each mounted to a different vertebra and comprising an interface 400 configured to releasably support an associated optical tracker 500. In this configuration, multiple vertebrae can be tracked during a surgical intervention.

The interface 400 of each tracker 500 is located on a side surface of the basis 110 and extends longitudinally in a direction parallel to longitudinal axes of the bodies 122 of the rotatably supported clamping members 120. The interface 400 may be releasably attachable to the basis 110. Each tracker 500 comprise four passive optical markers 510. Further, each tracker 500 is configured to removably receive a distal portion of the interface 400 of the bone clamp 100.

Removably attaching the interface 400 to the basis 110 and the tracker 500 to the interface 400 increases adaptability of each individual bone clamp 100 to the needs of a surgeon. Further, tracker registration may be facilitated. In particular, a registration of a first tracker 500 may be used for registration of a second tracker 500. After registration of the second tracker 500, the first tracker 500 may be removed to provide a less obstructive surgical space.

Figure 5:
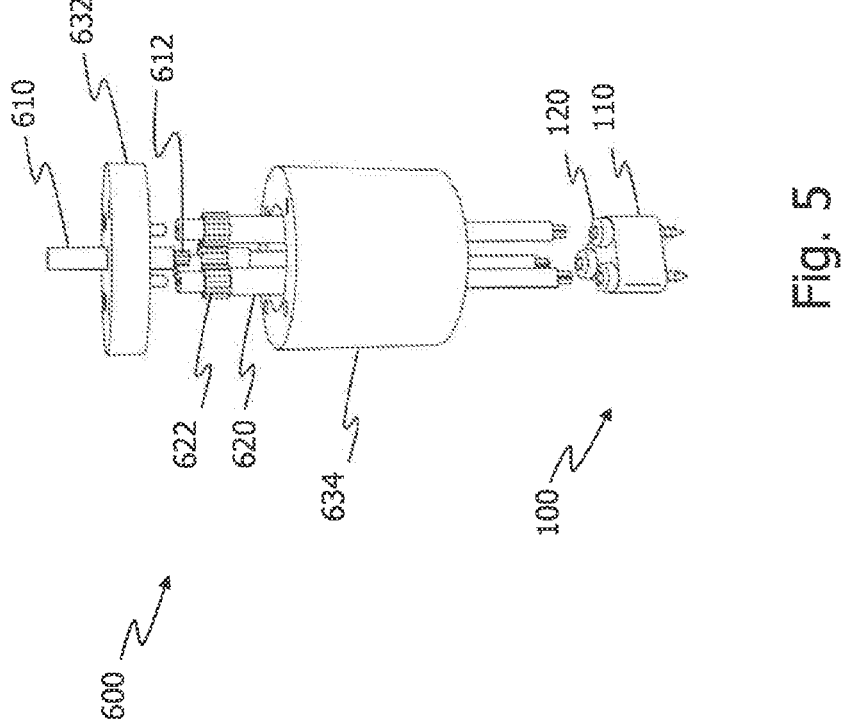
FIG. 5 illustrates a schematic representation of a bone clamp and a gear unit configured to operate the bone clamp.

FIG. 5 illustrates a schematic representation of a bone clamp 100 comprising multiple rotatably supported clamping members 120 and a gear unit 600 for simultaneously actuating the rotatably supported clamping members 120. The gear unit 600 comprises a single torque input structure 610 with a central sun gear 612 and multiple torque output structures 620 with associated planetary gears 622. The gear unit 600 comprises one torque output structure 620 for each of the rotatably supported clamping members 120, with each torque output structure 620. Each of the planetary gears 622 of the torque output structures is configured to mesh with the sun gear 612 of the torque input structure 610 to enable simultaneous rotation of the torque output structures 620 in response to an input torque. Each of the torque output structures 620 is further configured to engage one of the rotatably supported clamping members 120 in a torque-transmitting manner. Therefore, simultaneous rotation of the torque output structures 620 in response to an input torque results in a simultaneous rotation of the rotatably supported clamping members 120 when the torque output structures 620 engage the rotatably supported clamping members 120.

The gear unit 600 further comprises a housing 630 with an upper housing part 632 and a lower housing part 634. The upper and lower housing parts 632, 634 are shown spaced apart from each other to allow a better view of the gears 612, 622 of the torque input structure 610 and the torque output structures 620, respectively. In an assembled state, the upper and lower housing parts 632, 634 are removably attached to each other and abut each other (see FIG. 6). The housing 630 is configured to rotatably support the torque input and output structures 610, 620.

Figure 6:
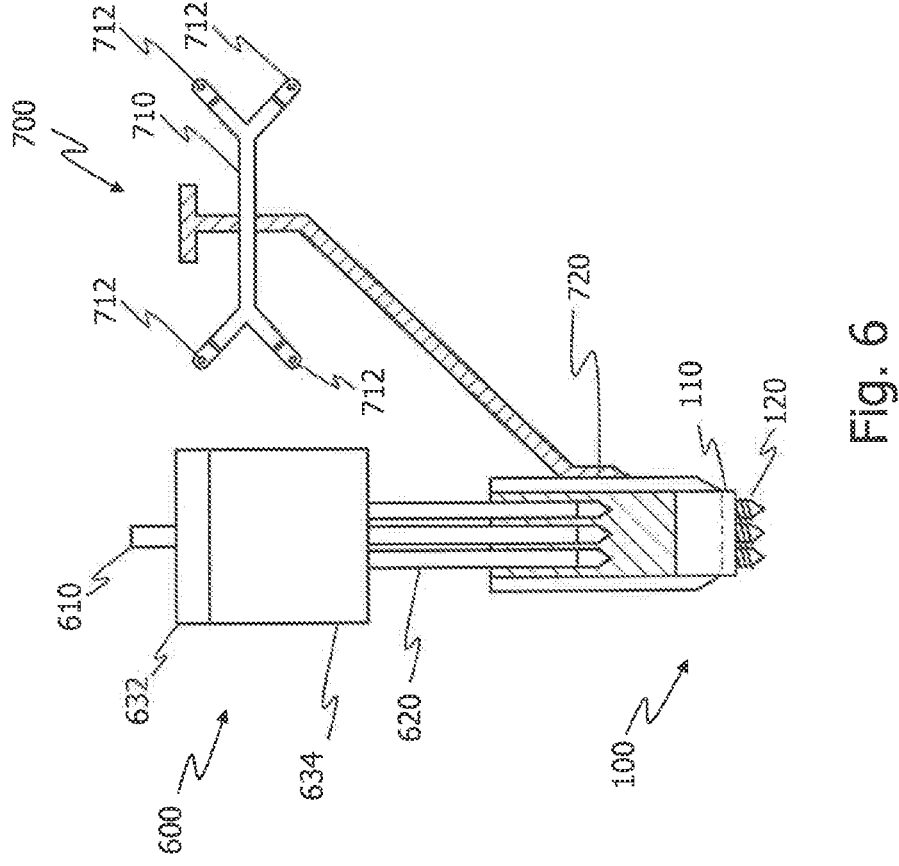
FIG. 6 illustrates a schematic representation of a bone clamp with a guiding member, a gear unit and a tracker.

FIG. 6 illustrates a schematic representation of a bone clamp 100 with a guiding member 200 and a gear unit 600 as described herein, and a tracker 700. The guiding member 200 is releasably attached to the bone clamp 100 and has a longitudinal axis extending parallel to the longitudinal axes of the rotatably supported clamping members 120 of the bone clamp 100. The guiding member 200 is configured for receiving the torque output structures 620 of the gear unit 600 and guiding them to the rotatably supported clamping members 120 of the bone clamp 100.

The tracker 700 comprises a first end 710 supporting four markers 712 and a second end 720 that is releasably or non-releasably attached to the guiding member 200. The second end 720 of the tracker 700 extends in a non-parallel manner relative to the longitudinal axes of the guiding member 200 to provide sufficient space for the gear unit 600. The gear unit 600 is shown with its housing 630 in the assembled state, i.e., with the upper and lower housing parts 632, 634 abutting each other and being releasably attached to each other.

Figure 7:
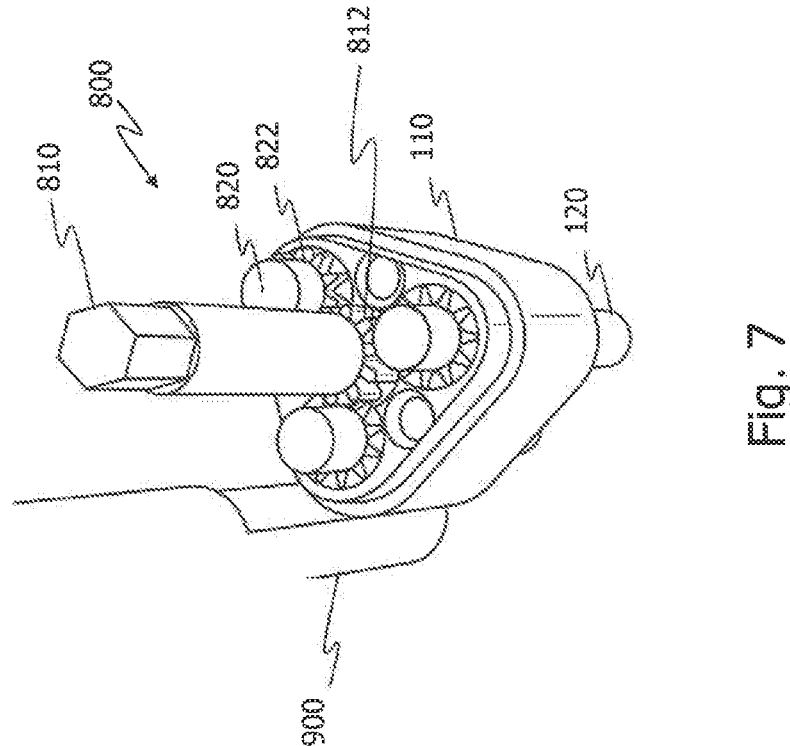
FIG. 7 illustrates a schematic representation of a gear unit for a bone clamp.

FIG. 7 illustrates a schematic representation of another realization of a bone clamp 100 integrally comprising a gear unit 800. Further, an interface 900 for receiving a tracker 300, 500, 700 is releasably attached to the basis 110.

The bone clamp 100 of FIG. 7 comprises a basis 110 with an upper part, i.e., a top, and lower part, i.e., a bottom (the upper part of the basis 110 is not shown in FIG. 7). The gear unit 800 comprises a single torque input structure 810 with a sun gear 812 and multiple torque output structures 820 with planetary gears 822. The gears 812, 822 are located within the basis 110 of the bone clamp 100. The torque input structure 810 extends through the upper part of the basis 110.

The basis 110 may releasably receive the torque input structure 810. In one example, the rotatably supported clamping members 120 may integrally comprise the planetary gears 822.

The bone clamp 100 comprising the gear unit 800 as shown in FIG. 7 provides a compact design that can be easily mounted to and dismounted from bone without the need of an external gear unit 600 for simultaneous actuation of the rotatably supported clamping members 120.

Figure 8:
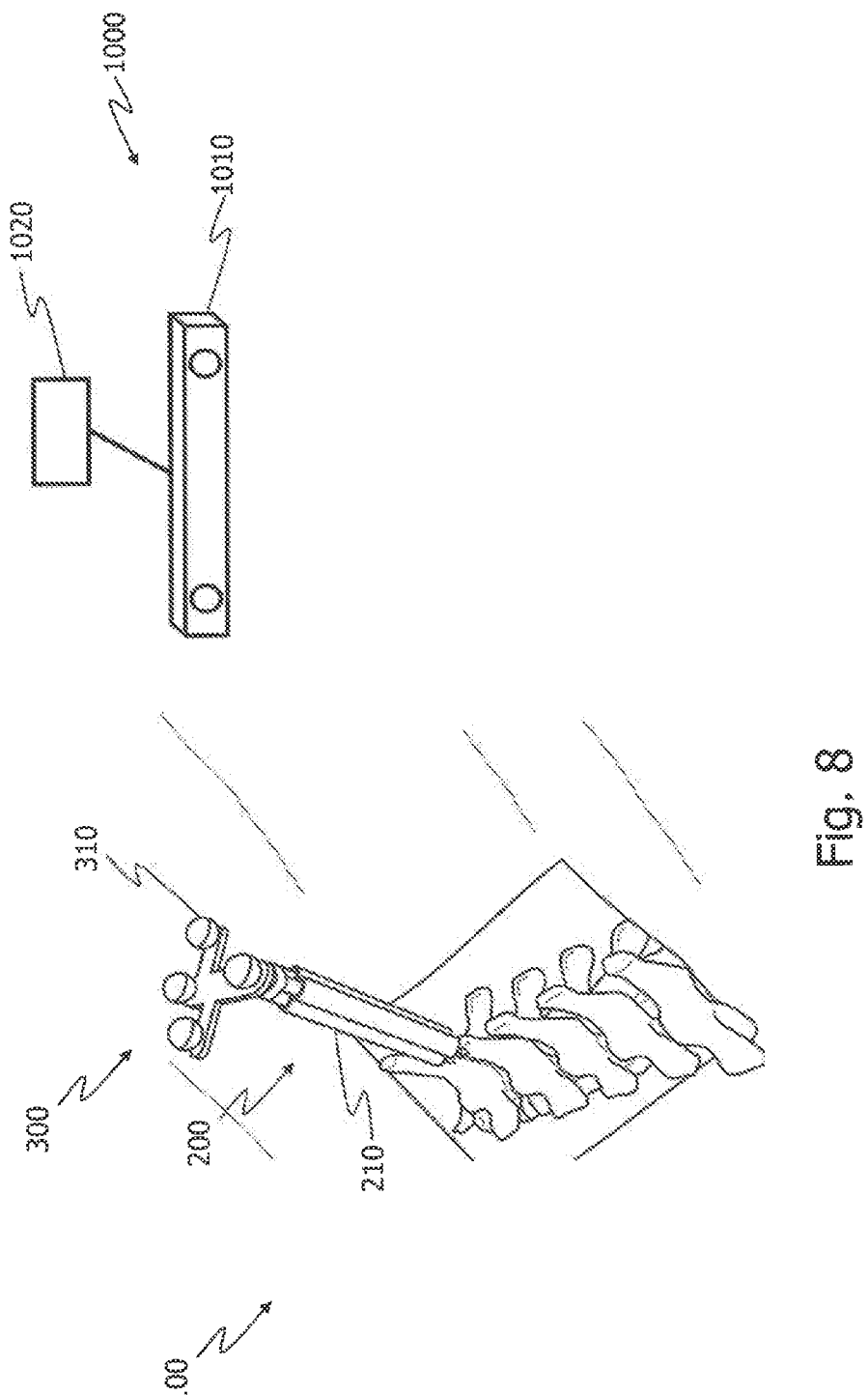
FIG. 8 illustrates a schematic representation of a surgical tracking system comprising the bone clamp and the optical tracker of FIG. 3B and a camera system.

FIG. 8 illustrates a schematic representation of a surgical tracking system comprising the bone clamp 100 with the optical tracker 300 of FIG. 3B and a camera system 1000. The camera system 1000 may be a camera system 1000 commonly used for optical tracking. The camera system 1000 shown in FIG. 8 comprises a stereo camera 1010 and a processor 1020 configured to receive and analyze image data from the stereo camera 1010 to track the tracker 300 in a dynamic reference system. In other examples, the camera system 1000 may comprise a mono camera or a combination of mono and stereo cameras. The camera system 1000 may be sensitive in an infrared spectrum. In the case of passive markers, the tracking system may further comprise a light source (e.g., an infrared light source).

In some variants, the tracking system may be an electromagnetic tracking system with a generator capable of generating an electromagnetic field. In such variants, the tracker may comprise one or more coils (e.g., integrated in the basis 110) configured to sense the electromagnetic field.

The invention claimed is:

1. A bone clamp comprising:
two or more clamping members configured to clampingly receive a bone therebetween;
a basis supporting at least two of the clamping members at a first distance to each other, wherein the at least two clamping members each have a body that is rotatably supported by the basis and a bone engaging structure extending helically along at least a part of a length of its body, wherein the bone engaging structure is configured to engage a surface of the bone upon rotation of the respective rotatably supported clamping member, wherein, depending on the direction of the rotation, the rotatably supported clamping member advances along the surface of the bone either in a downward direction for mounting the bone clamp or in an upward direction for dismounting the bone clamp; and
a gear unit having a single torque input structure and a torque output structure for each of the rotatably supported clamping members to simultaneously rotate each of the rotatably supported clamping members in response to an input torque.

2. The bone clamp of claim 1, wherein the first distance is selected such that the at least two clamping members can be brought into a clamping engagement with a bone from at least a first side and a second side of the bone.

3. The bone clamp of claim 2, wherein:
at least one of the rotatably supported clamping members is located on the first side of the bone and at least another one of the rotatably supported clamping members is located on the second side of the bone, and
the bone engaging structures of the rotatably supported clamping members located on the first and second sides of the bone are configured to engage the respective one of the first and second sides of the bone upon rotation of the respective rotatably supported clamping member.

4. The bone clamp of claim 1, wherein each of the at least two clamping members has a longitudinal axis, with the longitudinal axes of the at least two clamping members extending substantially parallel to each other.

5. The bone clamp of claim 1, wherein
each of the at least two rotatably supported clamping members has a longitudinal axis, with the longitudinal axes of the at least two clamping members extending substantially parallel to each other; and wherein
the bone clamp is configured to move in a direction parallel to the longitudinal axes of the at least two rotatably supported clamping members upon simultaneous rotation of the at least two rotatably supported clamping members.

6. The bone clamp of claim 1, wherein:
each of the at least two rotatably supported clamping members has a body with a longitudinal axis; and wherein
each of the at least two rotatably supported clamping members is configured to move relative to the basis in a direction parallel to the longitudinal axis of its body, when rotated.

7. The bone clamp of claim 1, wherein each of the at least two rotatably supported clamping members comprises a distal portion configured to receive at least a part of an actuation member configured to rotate the at least one rotatably supported clamping member.

8. The bone clamp of claim 1, wherein the body of each of the at least two rotatably supported clamping members comprises a tapering proximal portion.

9. The bone clamp of claim 8, wherein the body of each of the at least two rotatably supported clamping members comprises a cylindrical portion adjacent to the tapering proximal portion, wherein the bone engaging structure extends at least over a portion of the tapering proximal portion and the cylindrical portion.

10. The bone clamp of claim 1, wherein the basis is made of radiolucent material.

11. The bone clamp of claim 1, wherein the bone clamp comprises:
an interface configured for releasably engaging the gear unit.

12. The bone clamp of claim 1, wherein the interface configured for releasably engaging the gear unit comprises at least one fastening member configured to releasably engage at least one complementary fastening member of the gear unit, or vice versa.

13. The bone clamp of claim 1, further comprising:
one of a guiding member and an interface for receiving the guiding member, wherein the guiding member comprises a guiding tube for each of the at least one rotatably supported clamping members, each guiding tube being configured for guiding an actuation member to the respective rotatably supported clamping member.

14. The bone clamp of claim 1, wherein the bone clamp is configured to support an auxiliary device.

15. The bone clamp of claim 1, comprising one of:
a tracker of a surgical tracking system supported by the bone clamp; and
an interface configured to support the tracker.

16. The bone clamp of claim 1, wherein
one or more of the clamping members is integrally formed with the basis.

17. A surgical tracking system comprising:
a bone clamp comprising:
two or more clamping members configured to clampingly receive a bone therebetween;
a basis supporting at least two of the clamping members at a first distance to each other, wherein the at least two clamping members each have a body that is rotatably supported by the basis and a bone engaging structure extending helically along at least a part of a length of its body, wherein the bone engaging structure is configured to engage a surface of the bone upon rotation of the respective rotatably supported clamping member, wherein, depending on the direction of the rotation, the rotatably supported clamping member advances along the surface of the bone either in a downward direction for mounting the bone clamp or in an upward direction for dismounting the bone clamp, and wherein the bone clamp supports a tracker;

a sensor system configured to detect the tracker supported by the bone clamp; and a gear unit having a single torque input structure and a torque output structure for each of the rotatably supported clamping members to simultaneously rotate each of the rotatably supported clamping members in response to an input torque.

18. The surgical tracking system of claim 17, wherein the tracker is an optical tracker and the sensor system comprises an optical camera.

19. A method for detachably mounting a bone clamp to a bone, wherein the bone clamp includes:

two or more clamping members configured to clampingly receive a bone therebetween;

a basis supporting at least two of the clamping members at a first distance to each other, wherein the at least two clamping members each have a body that is rotatably supported by the basis and a bone engaging structure extending helically along at least a part of a length of its body, wherein the bone engaging structure is configured to engage a surface of the bone upon rotation of the respective rotatably supported clamping member; and a gear unit having a single torque input structure and a torque output structure for each of the rotatably supported clamping members to simultaneously rotate each of the rotatably supported clamping members in response to an input torque, the method comprising:

advancing the rotatably supported clamping member along the surface of the bone, depending on the direction of the rotation, either in a downward direction for mounting the bone clamp or in an upward direction for dismounting the bone clamp.

* * * * *